United States Patent [19]

McGroddy

[11] 4,117,726

[45] Oct. 3, 1978

[54] APPARATUS AND METHOD FOR SAMPLING WATER FOR FISH LARVAE AND OTHER TROPHIC LEVELS

[75] Inventor: Peter M. McGroddy, Suffern, N.Y.

[73] Assignee: Lawler, Matusky & Skelly Engineers, Tappan, N.Y.

[21] Appl. No.: 788,367

[22] Filed: Apr. 18, 1977

[51] Int. Cl.² .......................... G01N 1/10; A01K 79/00
[52] U.S. Cl. ..................................... 73/421 R; 43/6.5; 210/433 R
[58] Field of Search ............... 73/421 R, 421 B; 43/4, 43/6.5, 7; 119/3; 210/154, 433 R

[56] References Cited

U.S. PATENT DOCUMENTS

| 1,825,169 | 9/1931 | Wyckoff | 210/154 |
| 3,900,982 | 8/1975 | Gale | 43/7 |

Primary Examiner—S. Clement Swisher
Attorney, Agent, or Firm—Roy C. Hopgood; John M. Calimafde; Charles W. Neill

[57] ABSTRACT

This invention obtains samples of fish life in the larvae and egg stage and shortly thereafter, plankton and similar marine life. By taking samples before and after water has passed through cooling facilities of electric generating plants along a river, some of the effects of the power plant on the environment can be determined. The outstanding feature of this invention is that it collects the samples without passing the marine life through pumps in which much of it is killed or injured. Samples are collected in partially submerged equipment into which the water flows by gravity, and the water is discharged by pumps after the samples have been removed.

14 Claims, 6 Drawing Figures

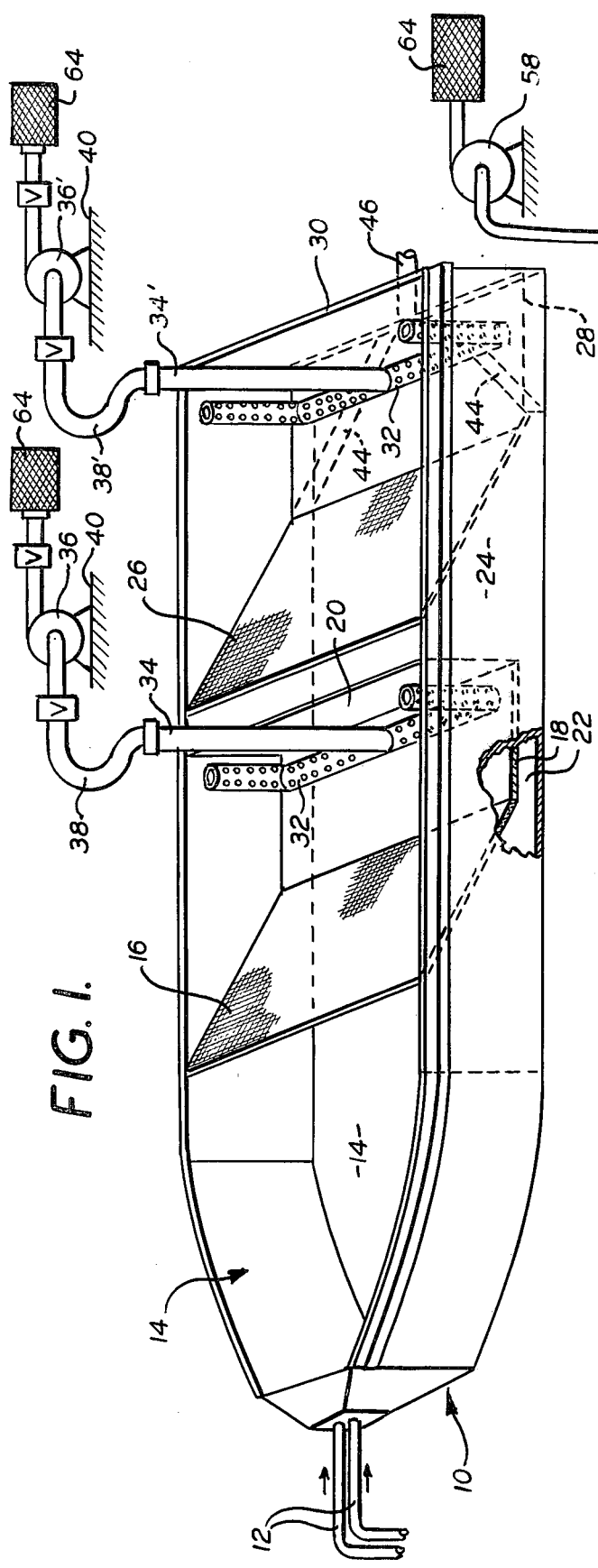
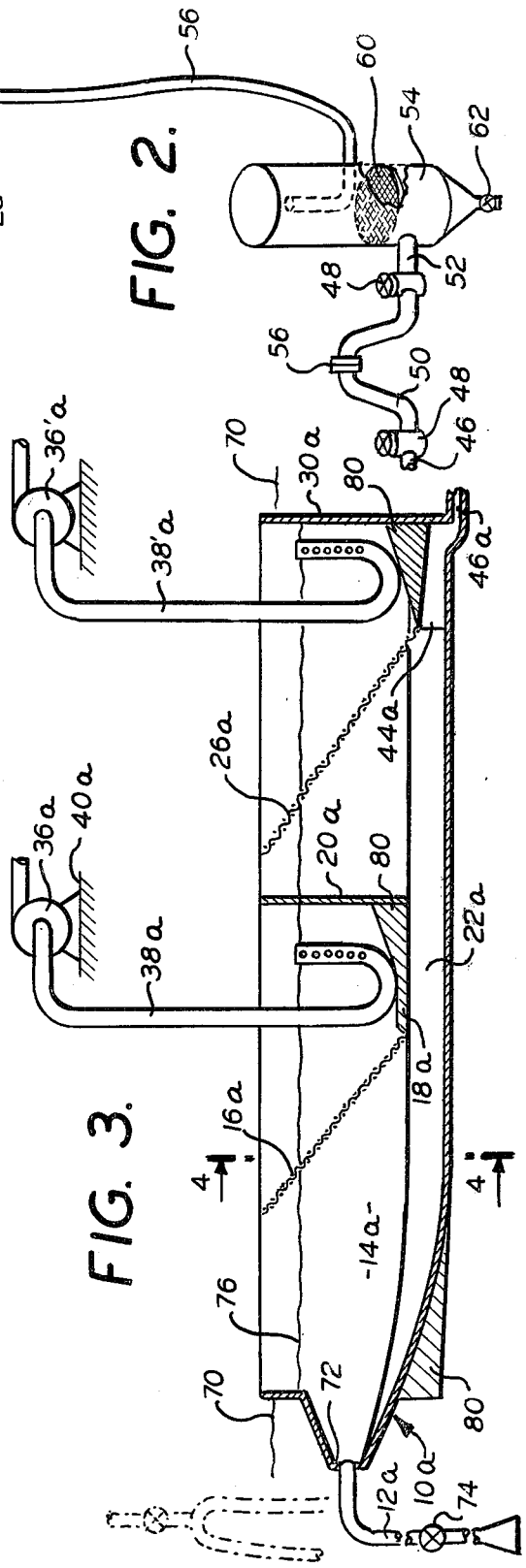

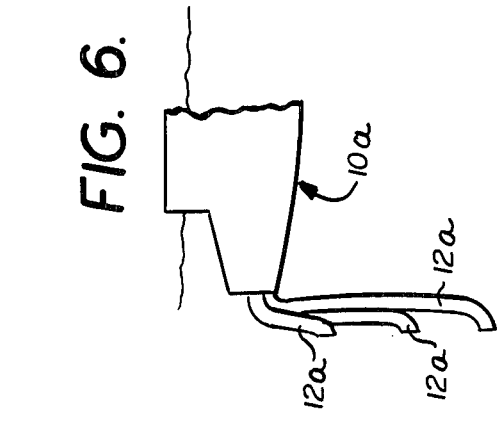
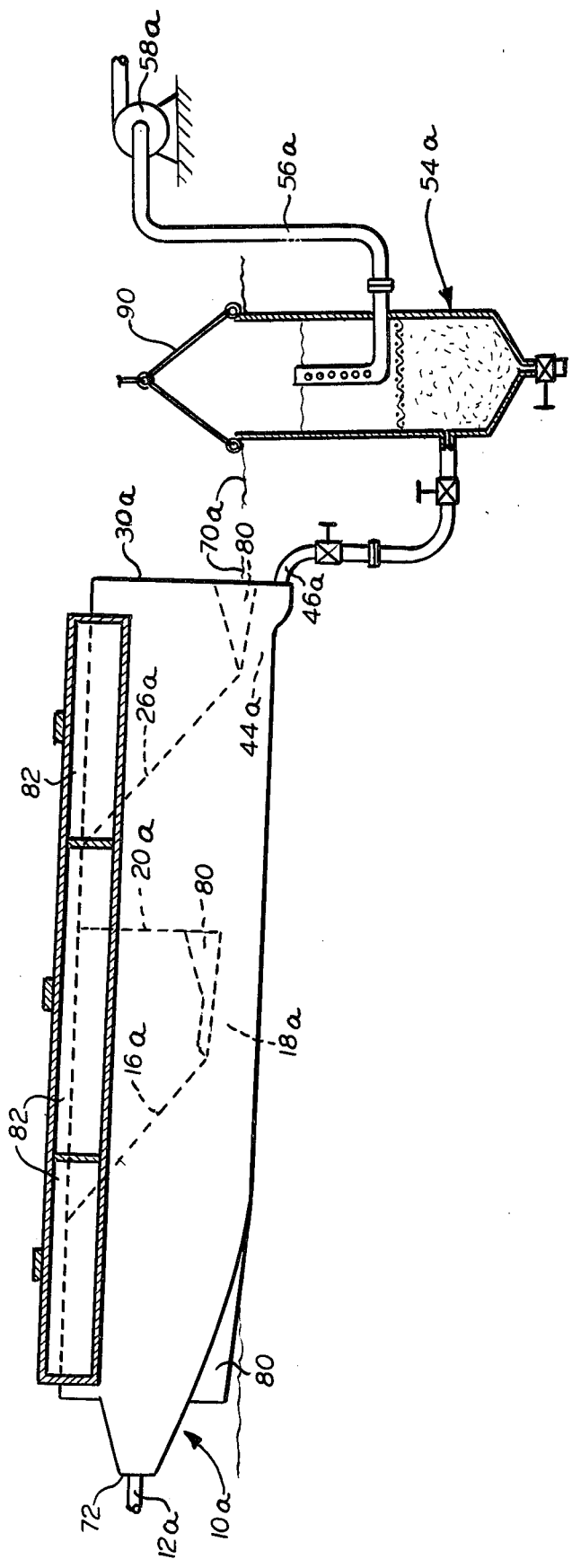

APPARATUS AND METHOD FOR SAMPLING WATER FOR FISH LARVAE AND OTHER TROPHIC LEVELS

BACKGROUND AND SUMMARY OF THE INVENTION

The obtaining of samples of fish larvae in rivers and other bodies of water is required for determining the condition of the river with respect to pollution, and environmental impact of electric generating stations and other equipment located along the river, and that require large quantities of water for use in their cooling apparatus.

The term "larvae" is used herein to designate fish life in its early stages, including egg, young fish with a yolk sac, and shortly thereafter, these being the times when the fish life is most delicate and likely to be destroyed by mechanical impact such as abrasion along a mesh seine and impact when passing through a pump.

The invention will be described as used for sampling water before and after it passes through the cooling equipment of a power plant, but it can be used for sampling measured quantities of river water (lakes and other bodies of water being considered the equivalent of rivers for purposes of this invention) to determine the concentration of the marine life at selected locations in the river.

In the past, conical nets of fine mesh, through which the samples of fish life did not pass, were dragged through the water to collect samples. The abrasion of the mesh against the larvae caused mechanical injury, and many of the samples were killed. Counts made were unreliable because there was no way of determining the number of larvae killed by the mesh and the number of dead larvae in the water before coming into contact with the mesh. Moving the conical net through the water at higher velocity resulted in destruction of greater numbers of the larvae.

Larger area screens, of fine mesh, were used in chambers where the velocity of the water could be made low as the result of the increase in net area; but pumps supplying the water to the chambers caused agitation fatal to some of the larvae and injurious to other parts of the sample. Even the use of recessed impellers for the pumps was insufficient to prevent injury to the samples by abrasion and impact.

This invention passes water through fine mesh partitions of large area and with resulting low water velocity; and preferably with two-stage separation to obtain more concentrated larvae in the samples of water collected. No pump is used until the larvae have been removed from the water; that is, the water is not pumped until after it has been passed through the mesh partition.

The preferred embodiment has the mesh partition in chambers that are at least partially submerged in the water from which the sample is to be taken, and the water flows into the chamber by gravity. Pumps beyond the chambers that have the mesh partitions are preferably carried by a support having no stiff connection with the chambers, and thus vibration of the pump and pump motors cannot reach the water samples. Flexible hoses connect the chambers, downstream of the mesh partitions, with the pumps.

Other objects, features and advantages of the invention will appear or be pointed out as the specification proceeds.

BRIEF DESCRIPTION OF DRAWINGS

In the drawing, forming a part hereof, in which like reference characters indicate corresponding parts in all the views:

FIG. 1 is a diagrammatic view of apparatus for collecting fish larvae in accordance with this invention;

FIG. 2 is a diagrammatic view of the collection vessels to which the concentrated samples are delivered from the second stage separation illustrated in FIG. 1;

FIG. 3 is a sectional view, through apparatus similar to FIG. 1, and illustrating the principle of operation without the use of pumps;

FIG. 4 is a sectional view taken on line 4—4 of FIG. 3;

FIG. 5 is an illustration of the way in which the water can be drained from the collection hull shown in FIG. 3; and FIG. 6 illustrates a modification of the invention for making open water abundance collections representing samples taken from a cross-section including different levels of a river or other body of water.

DESCRIPTION OF PREFERRED EMBODIMENT

FIG. 1 shows a vessel 10 containing a number of chambers. Water from which samples of fish larvae are to be taken enters the vessel 10 through water supply pipes 12 which open into a first chamber 14. Formerly, water samples were supplied to concentration chambers through pumps; but it is a feature of the present invention that the water enters the pipes 12 by gravity, as will be explained in connection with FIG. 3.

There is a mesh partition 16 extending across the full width of the chamber 14. The partition 16 preferably slopes downward in the direction in which the water flows through the vessel 10, and it is the instinct of the fish larvae to swim downwardly as they approach an obstruction such as the mesh partition 16. With the water moving at low velocity, there is less contact of fish larvae with the mesh as the result of the instinct of the larvae to move down into deeper water when threatened by contact with the screen 16 or other obstructions in the water.

The mesh of the partition 16 is chosen small enough to prevent larvae, of the size to be sampled, from passing through the partition 16.

The partition 16 does not extend all the way to the bottom of the chamber 14, and there is an inner bottom 18 extending from the lower end of the mesh partition 16 to an impervious bulkhead 20 which extends across the full width of the vessel 10 and which closes the part of the chamber 14 which is above the inner bottom 18.

Water which does not pass through the mesh partition 16 travels through a passage 22 formed by the bottom of the vessel 10 and the inner bottom 18. This water which passes through the passage 22 carries a concentration of fish larvae which move downward to escape contact with the mesh partition 16, and is discharged from the downstream end of the passage 16 into a second chamber 24, which has another mesh partition 26 similar to the mesh partition 16 and sloping downward in the same way as the partition 16 and for the same purpose.

At the lower end of the second mesh partition 26, there is an inner bottom 28; and this inner bottom 28 extends rearwardly to a transom 30 which forms the downstream end of the chamber 26.

Some fish larvae may make contact with the upstream surfaces of the mesh partitions 16 and 26; but the water which passes through these mesh partitions should contain no larvae of the type for which the mesh of the partitions 16 and 26 are intended to collect. Means are provided for pumping out the water which passes into the downstream end of the chambers 19 and 24. This means includes perforated pipes 32 extending across substantial cross-sections of the chambers 14 and 24; and exhaust pipes 34 and 34' connect with the perforated pipes 32 and draw water through the perforated pipes and from the downstream ends of the chambers 14 and 24.

In the preferred construction, there are pumps 36 and 36' connected with the exhaust pipes 34 and 34', respectively, by hoses 38 and 38'. The pumps 36 and 36' are driven by motors (not shown) and are preferably mounted on a stationary support 40, which may be a dock or other structure adjacent to the vessel 10 but not connected with the vessel. By making the hoses 38 and 38' flexible, and by having no rigid connection between the motor-driven pumps 36 and 36' and the vessel 10, the vibration of the pumps and motors is not transmitted to the vessel 10, and this avoids vibration of the mesh partitions 16 and 26 and any other parts of the vessel 10 with which fish larvae may be in contact.

The passage formed between the outer bottom of the vessel 10 and the inner bottom 28 has side walls 44 which converge toward the center of the lower end of the transom 30 so as to deflect the water and the fish larvae carried thereby, into an outlet pipe 46 which extends through the transom 30.

FIG. 2 shows the outlet pipe 46 with a valve 48, which is of special construction so that when it is in its open position it permits free flow of the water and fish samples without agitation or abrasion of the samples passing through the valve 48. A hose 50 connects the outlet pipe 46 with another pipe 52 through which the water and fish samples flow into a collector 54. The hose 50 has a quick disconnect coupling 56 and connects with a valve 48, similar to that on the pipe 46.

Water is withdrawn from the upper part of the collector 54 through a flexible hose 56 by a pump 58. There is a mesh partition 60 in the collector 54 for preventing any of the fish life from moving upward and out through the hose 56. There is a drain 62 at the lower end of the collector 54 with a closure, but with sufficient cross-section, when open, to discharge the concentrated fish life samples without injury to the fish life. It will be understood that new collectors 54 are attached to the hose 50 often enough to prevent excessive concentration of fish life in the collector 54 above levels which might be injurious to the fish life. As a check on the effective functioning of the mesh partitions 16, 26 and 60, there are cages 64 attached to the outlets of the different pumps 36, 36' and 58, with each of the cages having a mesh too small to permit passage of any of the fish life being sampled. Periodic inspection of the cages 64 determines whether any of the fish life is passing through the mesh partitions with the water which is pumped.

It is an important feature of this invention that no water is pumped until after the fish life, to be sampled, has been removed from the water. This is illustrated in FIG. 3. A vessel 10a is floated in a body of water from which fish life samples are to be taken. The vessel 10a floats low in the water; the water line being indicated by the reference character 70. Parts shown in FIG. 3, which correspond with parts shown in FIG. 1, are indicated by the same reference character with a letter "a" appended. A water inlet pupe 12a opens through portion 72 of the bow of the vessel 10a, and there is a valve 74 for controlling the flow of water through the pipe 12a into the chamber 14a. In FIG. 3, the vessel 10a is filled with water up to a water level indicated by the reference character 76. The rate at which water flows into the vessel 10a depends upon the vertical distance between the water in the river, as indicated by the reference character 70, and the water level 76 within the hull.

In order to prevent excessive velocity and eddy currents and possible abrasion of the fish life, the pipe 12a must be large enough, or additional pipes be used at the bow, to have the rate of flow moderate and the inside surface of the vessel 10a is preferably streamlined, as shown in FIG. 3, to insure smooth flow within the hull, and the difference in head between the levels 70 and 76 must be kept to a low value. The vessel 10a is shown with ballast 80 at various locations in the hull for making the hull float lower in the water, and external ballast control tanks 82 for adjusting the weight and buoyancy of the vessel 10a. The ballast control tanks are designed in sections divided by partitions to allow adjustment of the fore-to-aft trim of the vessel.

FIG. 4 shows the vessel 10a constructed with a chine 84 and a Vee bottom 86. This makes the passage 22a triangular in cross-section, which is different from the rectangular cross-section shown in FIG. 1. The pumps 36a and 36'a are connected by flexible hoses 38a and 38'a in the same way as in FIG. 1, though the connections are shown more diagrammatically in FIG. 3. FIG. 5 shows the use of the external ballast control tanks to accomplish drainage of the vessel 10a through the collector 54a. The drainage procedure is necessary to insure that all larvae are passed to the collector after inflow is terminated. Upon termination of inflow, pumps 36 and 36' are used to remove water to the level of pipes 32. The combination of buoyancy due to hull displacement and drainage of the ballast tanks causes the vessel 10a to rise causing gravity drainage of the contents to collector 54a. Parts in FIG. 5 which correspond to those shown in FIG. 2 are indicated by the same reference character with a letter "a" appended.

The collector 54a is shown floating, in FIG. 5, with the water level of the river indicated by the reference 70a, and the collector 74a is shown with cables 90 by which it can be lifted from the water. The hose 56a connects with a pump 58a which can be on a dock, as described in connection with FIGS. 1 and 2. However, if the vessel 10a is used at a location some distance from a dock, the pumps 36a and 36'a can be mounted on a support 40a which is located on another boat to prevent vibration of the pumps and motors from reaching the water and fish life in the vessel 10a. The same is true of the pump 58a (FIG. 5).

In taking samples for an open water abundance collection, it is necessary to take samples at different depths; and for an average sample, the vessel 10a can be equipped with a number of separate collector pipes 12a which open through adjacent openings across the bow and each of which extends downward for a different distance below the surface of the water.

The preferred embodiments of the invention have been been illustrated and described, but changes and modifications can be made and some features can be used in different combinations without departing from the invention as defined in the claims.

What is claimed is:

1. Apparatus for collecting fish larvae and other trophic levels without damage to the larvae by passage through a pump, said apparatus including in combination a chamber into which water containing the larvae flows, a fine mesh partition at one end of the chamber and through which water passes, the mesh being too fine to permit passage of the larvae to be collected so that the larvae become concentrated in the water that has not yet passed through the mesh, the mesh partition sloping downward in the direction in which the water flows toward the mesh partition, the partition being in such position that water passes upward through the mesh partition, a passage through which water containing concentrated larvae flows from the chamber to a collection region, and means for reducing the pressure in the chamber, on the upstream side of the mesh partition, below that of the water from which the larvae are collected, so that water flows into the chamber freely without passing through a pump, and means for reducing the water pressure on the downstream side of the mesh partition to obtain a controlled rate of flow through the mesh partition.

2. Apparatus for collecting fish larvae and other trophic levels without damage to the larvae by passage through a pump, said apparatus including in combination a chamber into which water containing the larvae flows, a fine mesh partition at one end of the chamber and through which water passes, the mesh being too fine to permit passage of the larvae to be collected so that the larvae become concentrated in the water that has not yet passed through the mesh, a passage through which water containing concentrated larvae flows from the chamber to a collection region, and means for reducing the pressure in the chamber below that of the water from which the larvae are collected, so that water flows into the chamber freely without passing through a pump, characterized by a vessel in which the chamber is contained, said vessel being partially submerged to a predetermined water line in the body of water from which the water containing the larvae flows into the chamber, and a water pump that draws water from the chamber, on the downstream side of the mesh partition, at a rate that maintains the water level in the chamber at a lower level than the water line to which the vessel containing the chamber is submerged.

3. The apparatus described in claim 2 characterized by the vessel containing the chamber being a hull that floats in said body of water, and means for causing the water pump to operate and withdraw water from within the hull at a rate fast enough to keep the hull afloat during the collection of a predetermined sample of larvae containing water.

4. The apparatus described in claim 3 characterized by means for regulating relative flow of water into and out of the hull to maintain a substantially constant water level for the hull during a period of collection of a predetermined quantity of water.

5. The apparatus described in claim 3 characterized by a passage through which water that has passed through the mesh partition is withdrawn from the downstream end of the chamber, the pump being located in position to suck water through said passage, a motor for driving the pump, supporting means for the pump and motor, said supporting means being remote from the hull to prevent vibration of the motor and pump from being transmitted through the supporting means to the hull and the water in the hull, the passage through which water passes from the hull to the pump containing a flexible section that stops mechanical vibration of the motor and pump from being transmitted through the passage to the water and larvae in the hull.

6. The apparatus described in claim 5 characterized by a second hull that floats in the body of water but spaced from the hull that contains the mesh partition, the pump and motor being supported by the second hull.

7. The apparatus described in claim 1 characterized by a control that determines the velocity of flow of water into the chamber and the rate of flow from the chamber of the water containing the concentration of larvae.

8. The apparatus described in claim 1 characterized by the passage for the water containing the concentration of larvae extending under the lower and most downstream edge of the mesh partition.

9. The apparatus described in claim 8 characterized by the portion of the chamber on the downstream side of the mesh partitions having a solid partition that separates the chamber from the passage through which the water containing the concentrated larvae flows from said chamber.

10. Apparatus for collecting fish larvae and other trophic levels without damage to the larvae by passage through a pump, said apparatus including in combination a chamber into which water containing the larvae flows, a fine mesh partition at one end of the chamber and through which water passes, the mesh being too fine to permit passage of the larvae to be collected so that the larvae become concentrated in the water that has not yet passed through the mesh, a passage through which water containing concentrated larvae flows from the chamber to a collection region, and means for reducing the pressure in the chamber below that of the water from which the larvae are collected, so that water flows into the chamber freely without passing through a pump, characterized by a second chamber into which the water containing the concentration of larvae flows, and in which there is a second fine mesh partition through which the water, but not the larvae, can pass for further concentration of the larvae in water that is withdrawn from the second chamber on the upstream side of the mesh partition, and means for withdrawing the water from the downstream side of the mesh partition of the second chamber and withdrawing water from the second chamber upstream from the mesh partition to a closed vessel.

11. The apparatus described in claim 10 characterized by a collection vessel into which water flows from the upstream side of the second mesh partition, the collection vessel having an outlet with a fine mesh screen for preventing passage of larvae but allowing escape of water from the collection vessel at low velocity.

12. The apparatus described in claim 3 characterized by the hull having a V bottom in which the passage of water with concentrated larvae flows, and a passage from the after end of the hull through which water in the V bottom can be drained from the hull when the hull is lifted to run water remaining in the hull out through an opening in the after end of the hull.

13. The apparatus described in claim 3 characterized by ballast in the hull and external ballast tanks for maintaining the fore-and-aft trim of the hull and located in positions to provide smooth flow of water within the hull from the bow toward the stern of the hull.

14. The apparatus described in claim 3 characterized by partitioned ballast control tanks on both sides of the hull and extending transversely outward therefrom at the approximate water line at which the hull is to be floated to provide a degree of difference between the water level outside and inside of the hull, and to provide a head of water for causing flow of water into the hull at velocities low enough to prevent any consequential damage to the larvae.

* * * * *